United States Patent [19]

Kirchner

[11] Patent Number: 5,022,487
[45] Date of Patent: Jun. 11, 1991

[54] STETHOSCOPE

[75] Inventor: Ulrich Kirchner, Narkgröningen, Fed. Rep. of Germany

[73] Assignee: Kirchner & Wilhelm GmbH & Co., Asperg, Fed. Rep. of Germany

[21] Appl. No.: 462,799

[22] Filed: Jan. 10, 1990

[30] Foreign Application Priority Data

Jan. 16, 1989 [DE] Fed. Rep. of Germany ... 8900402[U]

[51] Int. Cl.$^5$ ............................................. H04R 25/00
[52] U.S. Cl. .................................................... 181/137
[58] Field of Search ........................ 181/131, 137, 132

[56] References Cited

U.S. PATENT DOCUMENTS 3,690,404  9/1972  Collins .................................. 181/137
3,938,615  2/1976  Bodenger ......................... 181/137 X
4,669,572  6/1987  Fassbender ........................... 181/137

Primary Examiner—Brian W. Brown
Attorney, Agent, or Firm—Toren, McGeady & Associates

[57] ABSTRACT

A stethoscope includes a sound pickup and a reverberation chamber defined in a housing. The reverberation chamber is acoustically connected to binaurals through a connecting tubing. The reverberation chamber includes at least one sound inlet opening and the sound pickup includes at least one sound outlet opening, wherein at least one sound outlet opening and at least one sound inlet opening are arranged so as to be at least partially overlapping. The relative position of the at least one sound inlet opening and the at least one sound outlet opening is adjustable.

6 Claims, 1 Drawing Sheet

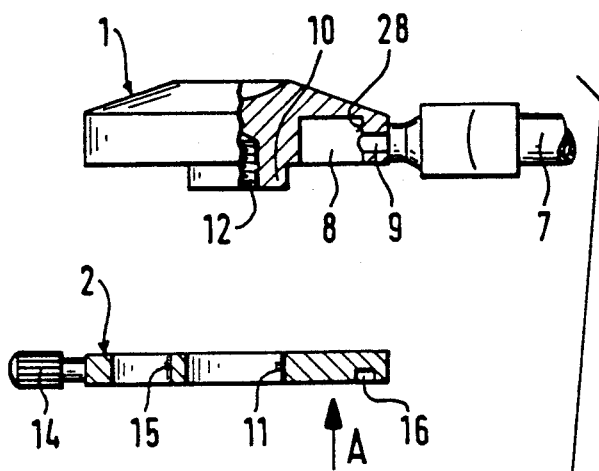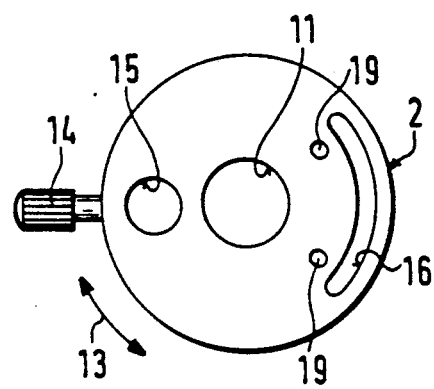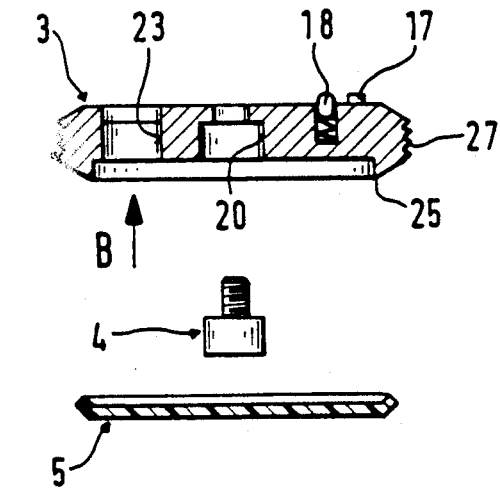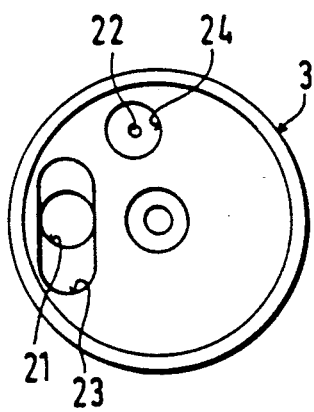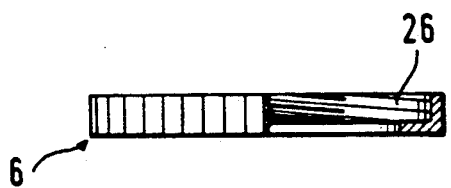
Fig. 1
Fig. 2
Fig. 3

STETHOSCOPE

BACKGROUND OF THE INVENTION

1. Field of the Invention

The present invention relates to a stethoscope with a sound pickup and a reverberation chamber in a housing. The reverberation chamber is acoustically connected to binaurals through a connecting tubing.

2. Description of the Related Art

A stethoscope is used by placing the sound pickup in the known manner on the body of a patient and picking up the acoustic sound waves produced by the body. These sound waves are conducted through the housing to the connecting tubing and finally to the binaurals. Sound waves of different frequencies are generated in dependence on the location of the body being listened to or the organ being examined. It is apparent that a stethoscope which has only one sound pickup is essentially only designed in an optimum manner for one frequency or a limited frequency range. For this reason, it was proposed in the past to equip a stethoscope with two sound pickups which can be optionally acoustically connected to the connecting tubing and, thus, to the binaurals. Accordingly, it is now possible to adjust the stethoscope to two frequencies or frequency ranges.

However, it has been found that it would be desirable if an adjustment could be carried out to more than two frequencies or frequency ranges without changing components of the stethoscope.

It is, therefore, the primary object of the present invention to further develop a stethoscope of the above described type, so that it can be easily adjusted to a certain sound frequency or frequency range without changing its individual components.

SUMMARY OF THE INVENTION

In accordance with the present invention, the reverberation chamber is provided with at least one sound inlet opening and the sound pickup is provided with at least one outlet opening, wherein at least one sound outlet opening and at least one sound inlet opening are arranged or arrangeable so as to be at least partially overlapping.

Thus, the reverberation chamber of this stethoscope is always in communication through a passage with the connecting tubing. Since the reverberation chamber has at least one sound inlet opening and the sound pickup has at least one sound outlet opening, at least one sound outlet opening can be arranged in relation to at least one sound inlet opening in such a way that the openings partially overlap or that the openings are in alignment to provide the full cross-sectional area. If several sound inlet openings and sound openings are provided, it must be ensured that at least always one passage exists for the sound waves from the sound pickup to the reverberation chamber and the passage must be adjusted in dependence on the frequency to be picked up to the maximum available cross-sectional area or to a reduced effective cross-sectional area. Of course, it is also possible that, for example, a passage having the full cross-sectional area is provided and additionally another passage with reduced cross-sectional area is provided at a different location.

The stethoscope can be adjusted by the manufacturer to a passage from the sound pickup to the reverberation chamber having a certain cross-sectional area or total cross-sectional area, so that the stethoscope is particularly suitable for a certain frequency or a certain frequency range.

Thus, in accordance with a further development of the invention, the relative position of the sound inlet opening as compared to the corresponding sound outlet opening is adjustable. This can be achieved by moving the sound inlet opening relative to the sound outlet opening or vice-versa. If several sound inlet openings and/or sound outlet openings are provided, the adjustment is carried out in the same manner. Accordingly, the effective cross-sectional area of the passage from the sound pickup to the reverberation chamber can be adjusted to the requirements or the respective case of application. The adjustment of the cross-sectional area of the passage is preferably continuous.

In accordance with another development of the invention, the reverberation chamber includes a housing cover in which the sound inlet opening or openings are provided. The housing cover is rotatably mounted on a housing base member. The housing cover is provided between the base member and the sound pickup and the sound pickup is connected rigidly with respect to rotation to the base member. As a result, the housing cover and the sound pickup essentially form a rotary slide valve which can be adjusted prior to or even during the use of the stethoscope in order to adjust the stethoscope in an optimum manner to the examination being carried out. The rotatable arrangement of the housing cover relative to the sound pickup in accordance with this development of the invention provides the advantage that the sound pickup can remain on the body of the patient while the stethoscope is adjusted and the sound pickup does not perform a movement relative to the body during adjustment.

In accordance with a preferred feature of the present invention, the rotary movement of the housing cover is limited by a circular arc-shaped receiving means and a stop member engaging the receiving means. In particular, the receiving means is provided in the housing cover and the stop member is provided in the sound pickup. The size of the angle of rotation depends primarily on the size of the sound inlet opening and of the sound outlet opening. The angle of rotation should be selected in such a way that a transition is possible from a completely released sound inlet opening to an essentially completely blocked sound inlet opening. If several openings are arranged next to each other in the direction of rotation, the angle of rotation must be appropriately larger in order to make it possible to transfer from one opening to the next opening.

The two end positions of the rotary movement are advantageously fixable by means of a snap member and two snap receiving means, wherein the snap member is spring biased and is preferably mounted on the sound pickup and the snap receiving means are provided on the housing cover.

The rotatably mounted housing cover can be provided with a knurling and/or, in accordance with a further development of the invention, with a preferably radially projecting handle for rotating the housing cover.

In accordance with another feature of the present invention, the housing cover has a sound inlet opening and the sound pickup has two sound outlet openings with different cross-sections, wherein the inside width of the larger sound outlet opening corresponds approximately to the inside width of the sound inlet opening.

In a stethoscope having conventional dimensions and circular sound inlet and sound outlet openings, the larger sound outlet opening usually has a diameter of approximately 1 cm, while the smaller sound outlet opening has a diameter of approximately 1 mm. However, these dimensions are preferred dimensions and can be selected differently without departing from the scope of the invention.

In accordance with another preferred embodiment of the present invention, the two sound outlet openings of the sound pickup are arranged offset in circumferential direction of the housing cover in such a way that the smaller sound inlet opening is acoustically connected to the sound inlet opening approximately when the larger sound outlet opening is at least substantially closed by the housing cover.

Thus, when the larger sound opening of the sound pickup completely releases the sound inlet of the housing in a first initial position and the cross-sectional area of the opening is continuously reduced by turning the housing cover, the openings can be arranged in such a way that, when a minimum effective cross-sectional area of the passage exists, a further turning of the housing cover in the same direction of rotation results in a release of the second inlet opening of the housing cover before the first inlet opening is completely closed. It is possible in this manner to achieve an essentially continuous transition from the largest to the smallest effective cross-sectional area of the passage.

In accordance with another development of the invention, at least the smallest outlet opening, but preferably both sound outlet openings, are shaped at their ends facing away front the housing cover so as to widen in the shape of a funnel. This has the result that the sound is better conducted to the actual openings or bores.

The sound pickup is preferably a diaphragm piece, i.e., the sound pickup includes in the known manner a particularly metal, plate-shaped member which defines a sound outlet opening or openings, a ring screwed onto the base member and diaphragm clamped between the base member and the ring.

The various features of novelty which characterize the invention are pointed out with particularity in the claims annexed to and forming a part of this disclosure. For a better understanding of the invention, its operating advantages and specific objects attained by its use, reference should be had to the drawing and descriptive matter in which there is illustrated and described a preferred embodiment of the invention.

BRIEF DESCRIPTION OF THE DRAWING

In the drawing:

FIG. 1 is an exploded view of the essential components of a chest piece or stethoscope head, shown in vertical section or in partial section;

FIG. 2 is a top view of the housing cover in the direction of arrow A of FIG. 1; and FIG. 3 is top view of the plate-shaped base member seen in the direction of arrow B of FIG. 1.

DESCRIPTION OF THE PREFERRED EMBODIMENT

As shown in FIG. 1 of the drawing, the stethoscope head includes essentially a housing base member 1, a housing cover 2, a plate-shaped base member 3, a fastening screw 4, a diaphragm 5 and a screw ring 6. A connecting tube 7 is connected to the housing base member 1 which is a conventional double tube or is forked at the end away from the stethoscope head, wherein the two ends of the tubes are connected to binaurals. The acoustic connection to the connecting tube 7 from the interior of a reverberation chamber 8 and the connection to the known binaurals is effected through a transverse bore 9 of the housing base member 1.

The housing base member 1 has a central bearing pin 10 for the housing cover 2 which is a circular disk with holes. The bearing pin 10 has a diameter which is reduced in a step-like manner towards the outside. A central bore 11 of the housing cover 2 provides an appropriate bearing play and corresponds approximately to the outer diameter of the free end of the bearing pin having the reduced diameter.

As further shown in FIG. 1 of the drawing, the bearing pin 10 has a central threaded bore 12. A fastening screw 4 is screwed into the bore 12 after the housing cover 2 and the plate-shaped base member have been previously mounted on the housing base member 1. The play in axial direction is selected in such a way that, when the screw 4 is tightly screwed in, the housing cover 2 can still be easily rotated in the direction of double arrow 13. The rotation is effected by means of a radially projecting pin-like handle 14 whose outer circumference is preferably knurled.

As illustrated in FIG. 2 of the drawing, a sound inlet opening 15 is provided laterally of the central bore 11 of the housing cover 2. A circular arc-shaped receiving means 16 for a stop member 17 of the plate-shaped base member 3 is arranged preferably offset by 180° relative to the sound inlet opening 15. The receiving means 16 and the stop member 17 form a means for limiting the rotary movement of housing cover 2.

The two end positions of rotation of the housing cover 2 can additionally be locked by means of a snap member 18 wherein the snap member 18 is spring-biased and is preferably provided on the plate-shaped base member 3, while the corresponding snap receiving means 19 are provided in the surface of the housing cover which faces away from the housing base member 1. The snap receiving means and the circular arc-shaped receiving means 16 are merely recesses, i.e., a flow therethrough is not possible. The plate-shaped base member 3 has a central fastening bore 20 whose diameter corresponds to that of the screw 4. The plate-shaped base member 3 additionally has a larger sound outlet opening 21 and a smaller sound outlet opening 22. These openings are two bores having different diameters. Both openings widen funnel-like toward the diaphragm 5, as indicated at 23 and 24, respectively. The opening 22 is truncated cone-shaped, while the opening 21 essentially has the shape of a truncated cone which is bulged in on two sides. In addition, the plate-shaped base member 3 has a rim 25 for placing the diaphragm 5 thereon. The diaphragm 5 is pressed against the rim 25 by means of screw ring 6. The screw ring 6 has a conventional internal thread 26, while the plate-shaped base member has an external thread 27.

In the illustrated embodiment of the invention, the sound outlet openings 21 and 22 and the sound inlet opening 15 are dimensioned and arranged in such a way that, when the smaller sound outlet opening 22 is completely released, the larger sound opening 21 is completely covered by the housing cover 2. The diameters of the openings 15 and 21 are approximately equal.

While a specific embodiment of the invention has been shown and described in detail to illustrate the application of the inventive principles, it will be understood that the invention may be embodied otherwise without departing from such principles.

I claim:

1. A stethoscope comprising a housing base member and a plate-shaped base member connected to the housing base member, the housing base member having a central bearing pin, a housing cover being rotatably mounted on the central bearing pin between the housing base member and the plate-shaped base member, the housing cover defining a sound inlet opening, means for limiting the relative rotation of the plate-shaped base member and the housing cover, the limiting means comprising a circular arc-shaped receiving means and a stop member engaging in the receiving means, the housing base member defining a reverberation chamber and a transverse bore in communication with the reverberation chamber, a connecting tubing connected to binaurals being attached to the housing base member and acoustically connected to the sound inlet opening of the housing cover through the transverse bore and the reverberation chamber in the housing base member, wherein the plate-shaped base member has two sound outlet openings which are offset in direction of rotation, the openings having diameters, wherein the two sound outlet openings have different diameters, wherein the sound outlet openings are alignable with the sound inlet opening by relative rotation of the housing cover and the plate-shaped base member, and wherein the diameter of the larger sound outlet opening of the plate-shaped base member corresponds essentially to the diameter of the sound inlet opening of the housing cover.

2. The stethoscope according to claim 1, wherein the circular arc-shaped receiving means is defined in the housing cover and the stop member is mounted on the sound pickup.

3. The stethoscope according to claim 1, comprising a radially projecting handle attached to the housing cover for turning the housing cover.

4. The stethoscope according to claim 1, wherein the two sound outlet openings of the sound pickup are arranged offset in circumferential direction of the housing cover, such that the smaller sound inlet opening is acoustically connected to the sound inlet opening approximately when the larger sound outlet opening is at least substantially closed by the housing cover.

5. The stethoscope according to claim 1, wherein the sound outlet openings have an end facing away from the housing cover, at least the smaller sound outlet opening having a funnel-like widening portion at the end facing away from the housing cover.

6. The stethoscope according to claim 1, wherein the sound pickup is a diaphragm piece.

* * * * *